United States Patent [19]

Hill et al.

[11] 4,131,732
[45] Dec. 26, 1978

[54] METHOD FOR PREPARING AURANOFIN

[75] Inventors: David T. Hill, North Wales; Blaine M. Sutton, Hatboro, both of Pa.; Ivan Lantos, Blackwood, N.J.

[73] Assignee: SmithKline Corporation, Philadelphia, Pa.

[21] Appl. No.: 789,603

[22] Filed: Apr. 21, 1977

[51] Int. Cl.$^2$ .............................................. C07H 5/10
[52] U.S. Cl. ...................................... 536/121; 536/4; 536/122
[58] Field of Search ............................ 536/4, 121, 122

[56] References Cited
U.S. PATENT DOCUMENTS 3,635,945   1/1972   Nemeth et al. ....................... 536/121

OTHER PUBLICATIONS

Sutton, "Jour. of Medicinal Chem." vol. 15, No. 11, 1972, pp. 1095–1098.
Noller "Chem. of Organic Cpds." 3rd Ed. W. B. Saunders, Co. Phila., Pa. 1965, pp. 304–307.

*Primary Examiner*—Johnnie R. Brown
*Attorney, Agent, or Firm*—William H. Edgerton

[57] ABSTRACT

A new synthesis of auranofin comprising reacting 2,3,4,6-tetra-O-acetyl-α-D-glucopyranosyl bromide with triethylphosphinegold(I) chloride and sodium or potassiumsulfide. Auranofin is an antiarthritic pharmaceutical compound. Auranofin is an orally active therapeutic agent which is useful in man as an antiarthritic.

5 Claims, No Drawings

METHOD FOR PREPARING AURANOFIN

This invention comprises a new chemical method for the preparation of auranofin which uses a 2,3,4,6-tetra-O-acetylglucopyranosyl reactive ester such as a bromide or chloride with triethylphosphine gold chloride in the presence of a monovalent alkali metal sulfide.

Auranofin is an orally active therapeutic agent which is useful in man as an anitarthritic [J. Med. Chem. 15, 1095 (1972); U.S. Patent No. 3,635,945].

The synthetic process here described and claimed is represented by the following diagram:

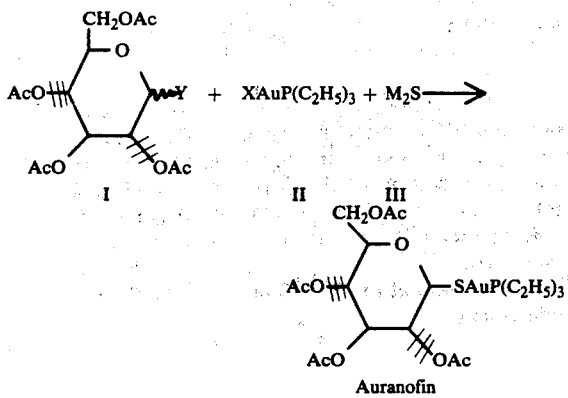

In this reaction sequence Y is a reactive ester residue leaving group such as a reactive halo for example bromo or chloro or an aryl or lower alkyl sulfonyloxy such as tosyloxy (toluenesulfonyloxy), brosyloxy (p-bromophenyl-sulfonyloxy), trifluoromethanesulfonyloxy or mesyloxy (methanesulfonyloxy); Ac is acetyl; M is a monovalent alkali metal such as potassium or sodium and X is a leaving group as defined by Y but is preferably chloro, bromo or iodo, Preferably for convenience Y is chloro or bromo and X is also chloro, bromo or iodo.

The configuration at the 1-position of the sugar starting materials (I) is indicated to be either $\alpha$ or $\beta$. Those skilled in the art will recognize that displacement of a $\alpha$-halo will give the desired $\beta$-configuration which is present in auranofin (SN2). The sulfur containing ester starting materials such as tosyloxy on the other hand will be in the $\beta$-configuration since one can expect no change in configuration upon reaction to give auranofin (SN1).

The term "leaving group" is that defined in the art as the weakly basic ionic group which is displaced by a nucleophilic group which in this case is the triethyl phosphinegoldthio group. See Organic Chemistry, Morrison and Boyd 3rd Ed. (1973). As defined above the leaving group is a reactive halo or sulfonyloxy moiety generated during the nucleophilic substitution.

The reaction is most conveniently carried out by reacting approximately equimolar quantities of a reactive 2,3,4,6-tetra-O-acetyl-$\alpha$-D-glucopyranosyl ester (I), a reactive triethylphosphinegold (I) halide (II) and either sodium or potassium sulfide (III) in a solvent system in which the reactants can be brought into contact. For example most conveniently an inert biphasic system of organic solvent/water may be used. The most commonly used organic solvent is a halogenated hydrocarbon solvent such as carbon tetrachloride, chloroform, methylene dichloride, ethylene tetrachloride or o-dichlorobenzene. Other water immiscible organic solvents may also be used such as benzenoid solvents such as benzene, toluene or xylene or hydrocarbon solvents such as cyclohexane. These give little advantage over the halogenated hydrocarbons.

An alternative which may be used is the addition of a phase transfer catalyst such as a Crown ether.

The conditions of the reaction may be varied by those skilled in the art but most usefully the reaction is carried out at about room temperature with stirring for from $\frac{1}{2}$-6 hours or until the reaction is complete. Heating up to the reflux temperature of the reaction may be used but with no marked advantage and in the case of high boiling solvents the reaction temperature may be limited to about 75°.

The starting materials for the reaction are known in the art for example a representative 2,3,4,6-tetra-O-acetyl-$\alpha$-D-glucopyranosyl halide, the bromide, is reported in Methods in Carbohydrate Chemistry, Vol. 2, page 434 (1963) R. L. Whistler et al. Others are prepared similarly. Representative tosyl, brosyl, trifluoromethane sulfonyl and mesyl esters are prepared for example from 2,3,4,6-tetraacetyl-$\beta$-glucose by the general reaction methods disclosed in Advances in Carbohydrate Chemistry, Vol. 8, Academic Press (1953) page 111. The tertiary-phosphinegold halides are reported in B. M. Sutton et al. J. Med. Chem. 15, 1095 (1972).

The reaction production is isolated by standard methods. For example the organic layer is separated washed and evaporated to give the desired crude auranofin which then may be purified by chromatography or fractional crystallization.

We assume that the alkali metal sulfide reacts initially with the tertiary-phosphinegold halide to give the sodium salt of the tertiary-phosphinegold thiol which in turn reacts with the sugar ester. We have no experimental evidence of this stepwise reaction sequence at this time.

The following examples are designed to teach the practice of this invention but not to limit its scope. All temperatures are Centigrade.

EXAMPLE 1

A mixture of 1.2 g (5 mmole) of sodium sulfide monohydrate in 20 ml of water was added to a mixture of 2.0 g (5 mmole) of 2,3,4,6-tetra-O-acetyl-$\alpha$-D-glucopyranosyl bromide and 1.7 g (5 mmole) of triethylphosphinegold(I) chloride in 20 ml of chloroform and 20 ml of water. After stirring at room temperature for 1 hour, the layers were separated. The chloroform layer was washed, dried over magnesium sulfate, filtered and the filtrate evaporated under reduced pressure to give oily crude auranofin. This material was passed over an alumina (Woehlm) column using chloroform to give solid auranofin which was then recrystallized from ethanol-water to give a white solid, m.p. 99–102° C. $[\alpha]_D^{25}$ (1% methanol) = $-52.4°$.

Substituting potassium sulfide and/or 2,3,4,6-tetra-O-acetyl-$\alpha$-D-glucopyranosyl chloride gives similar product. Methylene chloride may be substituted for chloroform.

EXAMPLE 2

A mixture of 3.4 g (10 mmole) of triethylphosphinegold(I) chloride with 10 mmole of 1-$\beta$-tosyloxy-2,3,4,6-tetra-O-acetylglucose and 10 mmole of potassium sulfide in 80 ml of methylene chloride — 30 ml of water is stirred at 0° C. for 1 hour then at room temperature for 5 hours. The organic layer is separated, washed, filtered and the filtrate evaporated to give crude auranofin which is purified as in Example 1.

Substituting the mesyloxy or brosyloxy esters in molar equivalent quantities gives the same product.

EXAMPLE 3

A chloroform solution (25 ml) of 1.0 g (1.5 mmole) of bis[(triethylphosphine)aurous]sulfide [Aust. J. Chem. 19, 547 (1966), prepared by reacting sodium sulfide with two mole equivalents of triethylphosphine chloride in chloroform-water] and 0.6 g (1.5 mmole) of 2,3,4,6-tetra-O-acetyl-α-D-glucopyranosyl bromide was stirred at room temperature for 48 hours. The solvent was removed at reduced pressure. The residue was purified over silica gel with benzene-ether (0 → 50%). The resulting product was crystallized from methanol-water to give auranofin, m.p. 109–111°, $[\alpha]_D^{25}$ (1% methanol) = −53.3°.

Alternatively the bromide in chloroform can be added to the chloroform-water mixture used to prepare the bis sulfide without isolating the sulfide.

What is claimed is:

1. The method of preparing auranofin comprising reacting a compound of the structure:

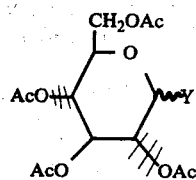

in which Ac is acetyl and Y is bromo, chloro, tosyloxy, brosyloxy, trifluoromethanesulfonyloxy or mesyloxy with sodium or potassium sulfide and triethylphosphinegold(I) chloride, bromide or iodide.

2. The method of claim 1 in which Y is a α-bromo or 2-chloro.

3. The method of claim 2 in which triethylphosphinegold(I) chloride is reacted with 2,3,4,6-tetra-O-acetylglucopyranosyl bromide in a biphase solvent system comprised of a halogenated hydrocarbon organic solvent and water until the reaction is complete.

4. The method of claim 1 in which methylene chloride is used.

5. The method of claim 3 in which methylene chloride is used.